US009226719B2

(12) United States Patent
Goto

(10) Patent No.: US 9,226,719 B2
(45) Date of Patent: Jan. 5, 2016

(54) X-RAY IMAGE DIAGNOSIS APPARATUS

(71) Applicant: Takahiro Goto, Nasushiobara (JP)

(72) Inventor: Takahiro Goto, Nasushiobara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 220 days.

(21) Appl. No.: 13/687,532

(22) Filed: Nov. 28, 2012

(65) Prior Publication Data

US 2013/0142303 A1 Jun. 6, 2013

(30) Foreign Application Priority Data

Dec. 2, 2011 (JP) .................................. 2011-264298

(51) Int. Cl.
*A61B 6/04* (2006.01)
*A61B 6/03* (2006.01)
*A61B 6/00* (2006.01)

(52) U.S. Cl.
CPC ............... *A61B 6/0407* (2013.01); *A61B 6/032* (2013.01); *A61B 6/0457* (2013.01); *A61B 6/542* (2013.01); *A61B 6/589* (2013.01)

(58) Field of Classification Search
CPC .... A61B 6/0407; A61B 6/032; A61B 6/0457; A61B 6/542; A61B 6/58–6/589
USPC ......................................................... 378/20
See application file for complete search history.

(56) References Cited

U.S. PATENT DOCUMENTS

2004/0202277 A1* 10/2004 Okumura et al. ............... 378/16
2008/0285712 A1* 11/2008 Kopans et al. ................. 378/26
2011/0274240 A1* 11/2011 Sugaya et al. .................. 378/16

FOREIGN PATENT DOCUMENTS

| CN | 1593343 A | 3/2005 |
| CN | 101856238 A | 10/2010 |
| JP | 7-124152 | 5/1995 |
| JP | 2005-080918 A | 3/2005 |
| JP | 2010-057731 A | 3/2010 |
| JP | 2010-214091 A | 9/2010 |

OTHER PUBLICATIONS

Combined Chinese Office Action and Search Report issued Jun. 9, 2014 in Patent Application No. 201210501676.X (with Japanese translation and English translation of categories of cited documents).

* cited by examiner

*Primary Examiner* — Jack Berman
*Assistant Examiner* — Eliza Osenbaugh-Stewar
(74) *Attorney, Agent, or Firm* — Oblon, McClelland, Maier & Neustadt, L.L.P.

(57) ABSTRACT

An X-ray image diagnosis apparatus according to embodiments includes: a table on which an examinee lies down; a table driving unit configured to move the table upward and downward; an imaging device configured to take a side image of the examinee by irradiating a side of the examinee on the table with X-rays and detecting X-rays transmitted through the examinee; and a controller configured to control the table driving unit so that the table driving unit moves the table upward or downward to make a center position of the examinee on the table in a thickness direction of the examinee coincide with a center position of the side image in an upward-downward moving direction of the table.

20 Claims, 5 Drawing Sheets

X-RAY IMAGE DIAGNOSIS APPARATUS

CROSS-REFERENCE TO THE RELATED APPLICATION

This application is based on and claims the benefit of priority from Japanese Patent Applications No. 2011-264298, filed on Dec. 2, 2011; the entire contents of which are incorporated herein by reference.

FIELD

Embodiments described herein relate generally to an X-ray image diagnosis apparatus.

BACKGROUND

An X-ray image diagnosis apparatus is an apparatus for obtaining tomographic images (slice images) of an examinee such as a patient by causing an X-ray irradiator to irradiate the examinee with X-rays, causing an X-ray detector to detect an amount of X-rays transmitted through the examinee, and performing reconstruction processing on X-ray transmission data which is based on the detected amount of X-rays. As an example of such an X-ray image diagnosis apparatus, an X-ray computed tomography (CT) apparatus has been developed. The X-ray CT apparatus is configured to image an examinee using an X-ray irradiator and an X-ray detector located opposite each other with the examinee in between, while rotating them about the body axis of the examinee.

In such an X-ray image diagnosis apparatus, generally, in order to set a scan field (imaging range) before imaging such as multislice scan or helical scan, scanograms are taken and collected by imaging the examinee without rotating the X-ray irradiator and the X-ray detector. Some X-ray image diagnosis apparatuses are provided with a function of calculating an optimum tube current supplied to the X-ray irradiator by using the scanograms (such a function is called, for example, Real-EC). With this function, an X-ray amount appropriate for the body thickness of each part of the examinee is automatically computed so as to allow detailed control of the X-ray amount for each rotation of the imaging device. Thereby, while maintaining the high image quality, unnecessary radiation exposure is suppressed to achieve reduction in radiation exposure.

However, the above function performs the computation assuming that the examinee is located at the center of an effective field of view (FOV). Actually, it is difficult to locate the examinee at the center of the effective field of view, and the positioning of the examinee is dependent on an operator. Thus, the reproducibility of examination is degraded.

DETAILED DESCRIPTION

According to one embodiment, an X-ray image diagnosis apparatus includes: a table on which an examinee lies down; a table driving unit configured to move the table upward and downward; an imaging device configured to take a side image of the examinee by irradiating a side of the examinee on the table with X-rays and detecting X-rays transmitted through the examinee; and a controller configured to control the table driving unit so that the table is moved upward or downward to make a center position of the examinee on the table in the thickness direction coincide with a center position of the side image in an upward-downward moving direction of the table.

An embodiment is described with reference to the drawings.

Figure 1:
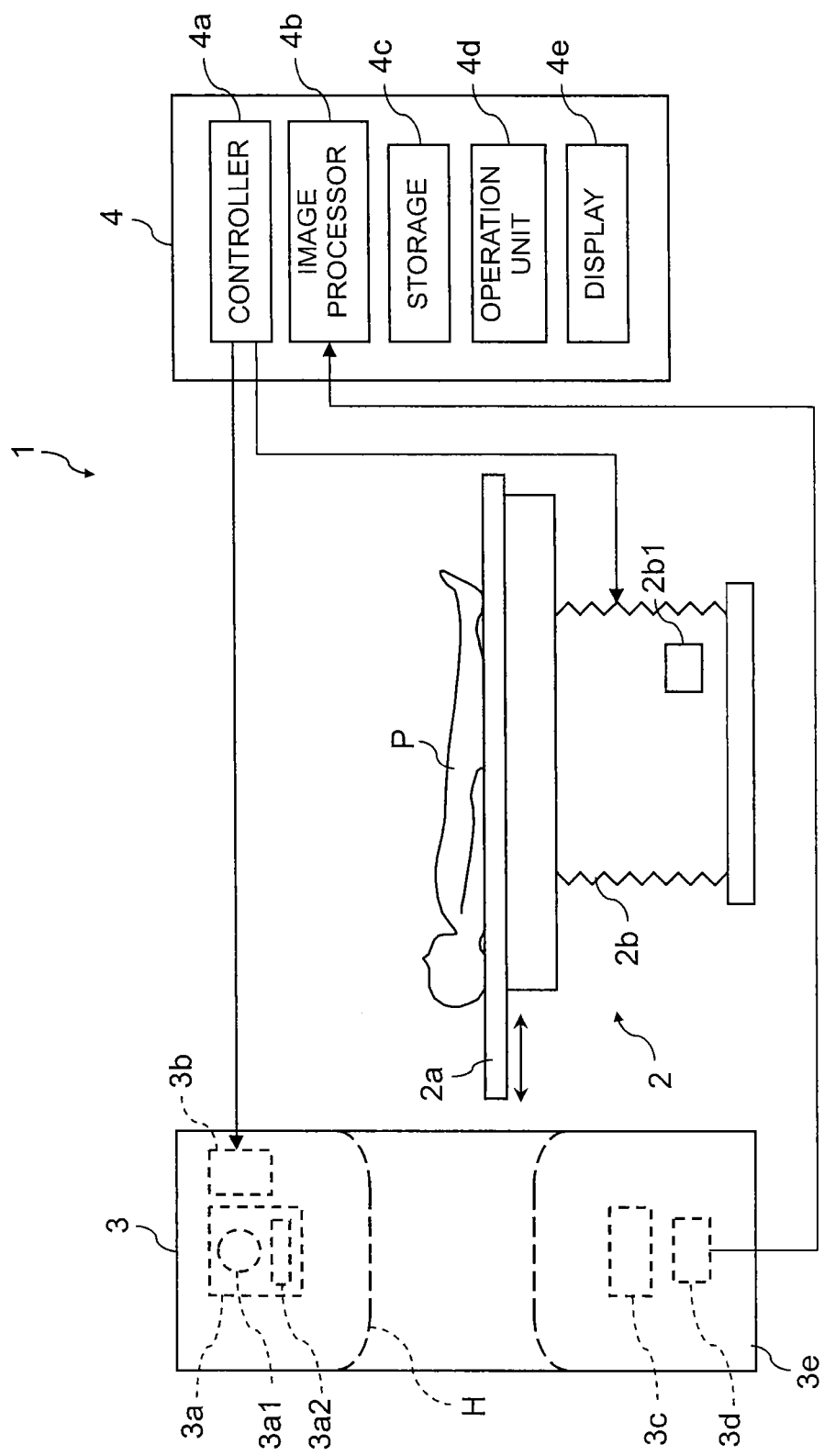
FIG. 1 is a diagram showing the schematic configuration of an X-ray image diagnosis apparatus according to one embodiment.

As shown in FIG. 1, an X-ray image diagnosis apparatus 1 according to this embodiment includes a bed 2 on which an examinee P such as a patient lies down, an imaging device 3 configured to image the examinee P on the bed 2, and a control device 4 configured to control the bed 2 and the imaging device 3. Examples of this X-ray image diagnosis apparatus 1 include an X-ray computed tomography (CT) apparatus.

The bed 2 includes a rectangular table 2a on which the examinee P lies down and a table driving unit 2b configured to move the table 2a horizontally or vertically (in an up-down direction) while supporting the table 2a. The table driving unit 2b has a moving mechanism for moving the table 2a, a power source for supplying driving power for moving table 2a, and the like. The table driving unit 2b of the bed 2 moves the table 2a to a desired height and then moves the table 2a horizontally to move the examinee P on the table 2a to a desired position.

The imaging device 3 includes an X-ray irradiator 3a configured to irradiate the examinee P on the table 2a with X-rays, a high-voltage generator 3b configured to supply a high voltage to the X-ray irradiator 3a, an X-ray detector 3c configured to detect X-rays, a data collector 3d configured to collect, as X-ray transmission data (projection data), the X-ray detected by the X-ray detector 3c, and a gantry 3e incorporated with these units.

The X-ray irradiator 3a is located inside the gantry 3e and includes an X-ray tube 3a1 from which X-rays are outputted and a narrowing device, such as a collimator, configured to narrow a beam of the X-rays outputted from the X-ray tube 3a1. In the X-ray irradiator 3a, the X-ray tube 3a1 outputs X-rays, and the narrowing device 3a2 narrows a beam of the X-rays into a fan-beam having a cone vertex, for example, a pyramid-shaped beam, which is then applied to the examinee P.

As the narrowing device 3a2, various types of narrowing device can be used. For example, the narrowing device may be a type in which two X-ray shielding plates made of lead or the like are moved toward or away from each other to appropriately change the size of a gap formed by the X-ray shielding plates. The gap part serves as an X-ray transmission area, and an area other than the gap part serves as an X-ray shielding area. The X-ray irradiation field (irradiation area) can be adjusted using such a narrowing device 3a2.

The high-voltage generator 3b is a device located inside the gantry 3e to generate a high voltage to be supplied to the X-ray tube 3a1 of the X-ray irradiator 3a. The high-voltage generator 3b boosts and rectifies a voltage given thereto by the control device 4, and supplies this voltage to the X-ray tube 3a1. The control device 4 is configured to cause the X-ray tube 3a1 to generate desired X-rays by giving an appropriate tube current to the X-ray tube 3a1, and therefore controls the waveform of a voltage to be given to the high-voltage generator 3b, i.e., controls various conditions such as the amplitude, pulse width, and the like of the voltage.

The X-ray detector 3c is located inside the gantry 3e at a position opposite the X-ray irradiator 3a. The X-ray detector 3c converts X-rays transmitted through the examinee P on the table 2a of the bed 2 into electric signals, and sends them to the data collector 3d. The X-ray detector 3c may employ either a direct conversion method in which X-rays are directly converted into electric signals or an indirect conversion method in which X-rays are first converted to optical information pieces, which are then converted to electric signals.

As the X-ray detector 3c, for example, a multilayered, multichannel X-ray detector can be used. The multislice, multichannel X-ray detector is configured with X-ray detection elements configured to detect X-rays and arranged in lattice. Specifically, a channel is formed by multiple (e.g., several hundreds to several thousands of) X-ray detection elements arranged in a channel direction (i.e., a direction about the body axis of the examinee P), and multiple (e.g., 16 or 64) rows of such a channel are arranged in a slice direction (i.e., in a direction of the body axis of the examinee P).

The data collector 3d collects the electrical signals sent from the X-ray detector 3c as X-ray transmission data (projection data), and sends this X-ray transmission data to the control device 4. The data collector 3d is located inside the gantry 3e.

The gantry 3e has a cylindrical hollow shape, and has a through-hole H into which the table 2a of the bed is inserted for examination of the examinee P. The gantry 3e has a rotational ring (not shown) which is a rotator rotating about the through-hole H. In this rotational ring, the X-ray irradiator 3a and the X-ray detector 3c are located at opposite positions, and rotation of the rotational ring causes the X-ray irradiator 3a and the X-ray detector 3c to rotate about the body axis of the examinee P on the table 2a of the bed 2.

The control device 4 includes components such as a controller 4a configured to control each unit, an image processor 4b configured to perform image processing, including image reconstruction, on the X-ray transmission data, a storage 4c configured to store various programs, various data, and the like, an operation unit 4d configured to receive an input operation from the operator, and a display 4e configured to display images. These units are electrically connected to each other via a bus line (not shown) or the like.

The controller 4a controls units such as the table driving unit 2b of the bed 2 and the high-voltage generator 3b of the imaging device 3. In addition, the controller 4a controls the narrowing device 3a2 of the X-ray irradiator 3a, and controls display of various images, such as X-ray images, on the display 4e. The controller 4a is also capable of obtaining information on the position (e.g., the height position) of the table 2a based on a value outputted from a table-position detector 2b1 (e.g., an encoder) provided to the power source (e.g., a servo motor) such as the table driving unit 2b.

The image processor 4b performs various types of image processing, such as preprocessing and image reconstruction processing, on the X-ray transmission data sent from the data collector 3d, and then saves the X-ray image obtained by the image processing in the storage 4c. For example, an array processor or the like can be used as this image processor 4b.

The storage 4c is a storage device configured to store various programs, various data, and the like, and particularly, stores X-ray images as the various data. The storage unit 4c is configured by a ROM, a RAM, a flash memory, a hard disk, or the like. Note that the X-ray images may be saved in an image server or the like connected to the control device 4 through a wired or wireless network.

The operation unit 4d is an input unit on which an operator inputs operations. The operation unit 4d is configured with, for example, a keyboard, a mouse, a control lever, and the like. The operator make inputs through the operating unit 4d to make various settings, to move the examinee P on the table 2a using the bed 2, or to perform imaging by the imaging device 3.

The display 4e is a display device configured to display various types of images, such as an X-ray image of the examinee P and an operation screen. For example, a liquid crystal display, a CRT-based display, or the like can be used as the display 4e.

The X-ray image diagnosis apparatus 1 configured as above has two imaging modes: a scanogram mode for taking a scanogram serving as an image for positioning and a tomographic mode (a regular scan mode) for taking tomographic images (slice images). In the scanogram imaging mode, prior to the imaging in the tomographic imaging mode, scanograms are taken to set a scan field (imaging range). For example, in a scan plan, scanograms are taken in advance, and they are displayed on the display 4e. The operator checks these scanograms, and sets a scan field by making input operations through the operation unit 4d.

The scanograms are each taken as follows. First, the X-ray irradiator 3a and the X-ray detector 3c are fixed at predetermined positions, namely, predetermined view angles. Then, the table 2a of the bed 2 is moved in a direction of the body axis of the examinee P to a predetermined position. The examinee P is irradiated with X-rays by the X-ray irradiator 3a, and the X-ray detector 3c detects X-rays transmitted through the examinee P on the table 2a. The data collector 3d collects X-ray transmission data thus obtained. Thereafter, the image processor 4b processes the X-ray transmission data to generate a scanogram, saves this generated scanogram in the storage 4c, and displays it on the display 4e.

Figure 2:
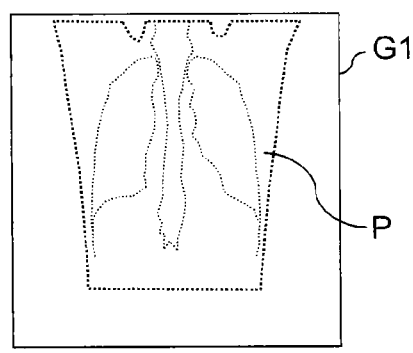
FIG. 2 is a diagram illustrating a plan scanogram taken by an imaging device of the X-ray image diagnosis apparatus shown in FIG. 1.
Figure 3:
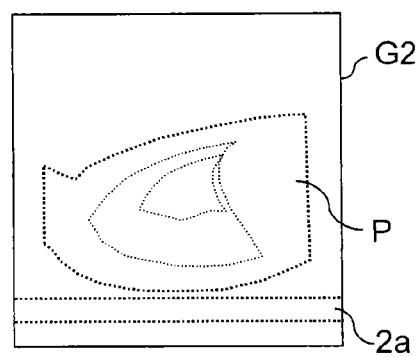
FIG. 3 is a diagram illustrating a side scanogram taken by the imaging device of the X-ray image diagnosis apparatus shown in FIG. 1.

For example, the scanograms are taken at positions with view angles of 0° (plan position) and 90° (side position). At this time, the irradiation field is set to maximum (e.g., 512 pixels×512 pixels) here, but is not limited to this. At the 0° plan position, X-rays are applied to the upper surface of the examinee P on the table 2a, and X-rays transmitted through the examinee P are detected. A plan image G1 as shown in FIG. 2 is thereby taken as a plan scanogram of the examinee P. At the 90° side position, X-rays are applied to the side of the examinee P on the table 2a, and X-rays transmitted through the examinee P are detected. A side image G2 as shown in FIG. 3 is thereby taken as a side scanogram. Note that the side image G2 includes an image of the table 2a as well.

On the other hand, the tomographic images are taken as follows. First, the X-ray irradiator 3a and the X-ray detector 3c are kept rotating. In that state, while the table 2a of the bed 2 is moved in the body axis of the examinee P, the examinee P is irradiated with X-rays by the X-ray irradiator 3a, and the X-ray detector 3c detects X-rays transmitted through the examinee P on the table 2a. The data collector 3d collects X-ray transmission data thus obtained. Thereafter, the image processor 4b processes the X-ray transmission data to generate tomographic images, saves these generated tomographic images in the storage 4c, and displays them on the display 4e.

Next, a detailed description is given of the controller 4a of the control device 4.

Figure 4:
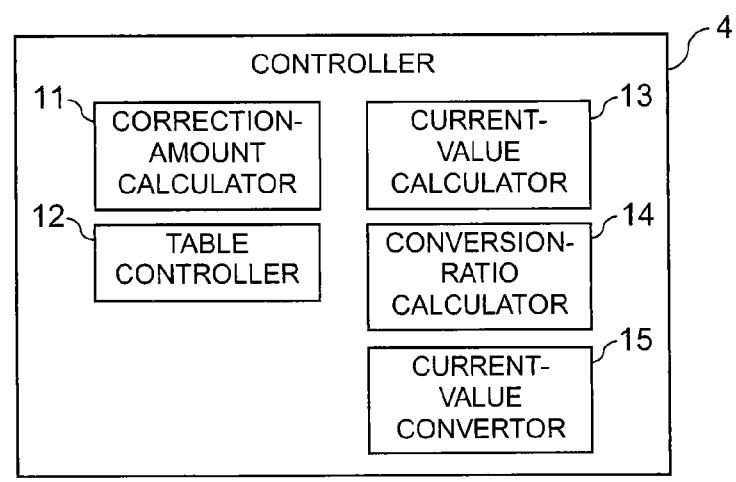
FIG. 4 is a block diagram showing the schematic configuration of a controller inside a control device of the X-ray image diagnosis apparatus shown in FIG. 1.

As shown in FIG. 4, the controller 4a includes a correction-amount calculator 11 configured to calculate an offset amount to be used as a correction amount, a table controller 12 configured to control upward and downward movement of the table 2a based on the calculated offset amount, a current-value calculator 13 configured to calculate a tube current (current value) to be supplied to the X-ray tube 3a1, a conversion-ratio calculator 14 configured to calculate a conversion ratio for converting the tube current, and a current-value convertor 15 configured to convert the tube current using the calculated conversion ratio.

The correction-amount calculator 11 obtains the height of the table 2a and the thickness of the examinee P by using the side image G2 (called an L-R (left-right) direction scanogram), and thus calculates an offset amount used to place the examinee P at the center of an FOV (effective field of view).

Figure 5:
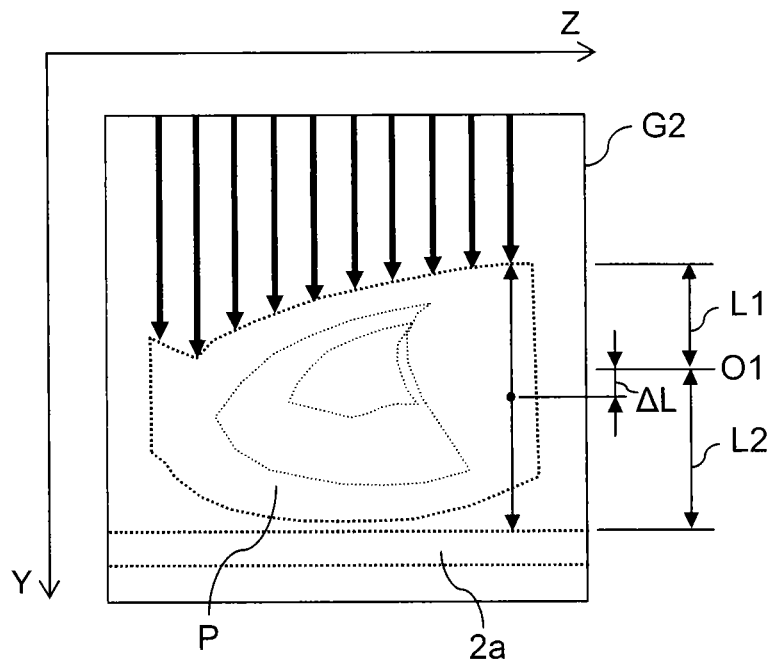
FIG. 5 is a diagram illustrating calculation processing for obtaining an offset amount from the side scanogram shown in FIG. 3.

As shown in FIG. 5, the correction-amount calculator 11 first bisects the side image G2 through an image center O1 which is a center in a Y direction (the upward-downward moving direction of the table 2a), and scans the upper half in the Y direction to calculate the number of pixels in an air region. This Y-direction scan is performed for each of pixel lines arranged in a Z direction (i.e., the direction of the body axis of the examinee P). A region with pixels at or below a given threshold is recognized as the air region. Next, the correction-amount calculator 11 subtracts the number of pixels in the air region from the number of pixels in the upper half to obtain the number of pixels from the image center O1 to the body surface of the examinee P. This calculation is carried out for each of the pixel lines arranged in the Z direction to obtain a maximum value L1 of the number of pixels from the image center O1 to the body surface.

As for the lower half, the correction-amount calculator 11 obtains the number of pixels from the image center O1 to the current height position of the table 2a. Then, the correction-amount calculator 11 acquires the current height position of the table 2a from the system (e.g., the encoder of the table driving unit 2b), determines to which pixels in the side image G2 the height position corresponds, and calculates the number of pixels L2 from the image center O1 to the table 2a.

Thereafter, the correction-amount calculator 11 obtains an examinee thickness by adding the maximum value L1 of the number of pixels from the image center O1 to the body surface and the number of pixels L2 from the image center O1 to the table 2a, and calculates an offset amount ΔL, or specifically, by how many pixels the center position of the examinee thickness in the thickness direction should be offset so as to be located at the center of the FOV.

Although the maximum value L1 of the number of pixels from the image center O1 to the body surface is used in the above calculation of the examinee thickness, the present invention is not limited to this. Instead, as an example, the mean value of the number of pixels may be used. Moreover, although the above processing is performed after bisecting the side image G2, the present invention is not limited to this. The processing may be performed without bisecting the side image G2, but the processing time can be shortened if the side image G2 is bisected.

The table controller 12 uses the offset amount ΔL calculated by the correction-amount calculator 11 to control the upward and downward movement of the table 2a so that the center position of the examinee P on the table 2a in the thickness direction may coincide with the image center O1 of the side image G2 (the center position of the side image G2 in the upward and downward moving direction of the table 2a). Specifically, the table controller 12 first converts the offset amount ΔL (in pixel) to a distance (in millimeter), and causes the table driving unit 2b to move the table 2a upward or downward by that distance.

For example, as shown in FIG. 5, when the center position of the examinee P in the thickness direction is located below the image center O1, the table 2a is moved upward by the offset amount ΔL. On the other hand, when the center position of the examinee P in the thickness direction is located above the image center O1, the table 2a is moved downward by the offset amount ΔL.

The current-value calculator 13 calculates an integrated value for each pixel line from the plan image G1 (called an AP-direction (front-rear direction) scanogram image) to calculate a tube current which allows a preset noise level. For example, the current-value calculator 13 calculates a lowest possible tube current by which all slice images can be displayed with the same S/N (SN ratio).

Figure 6:
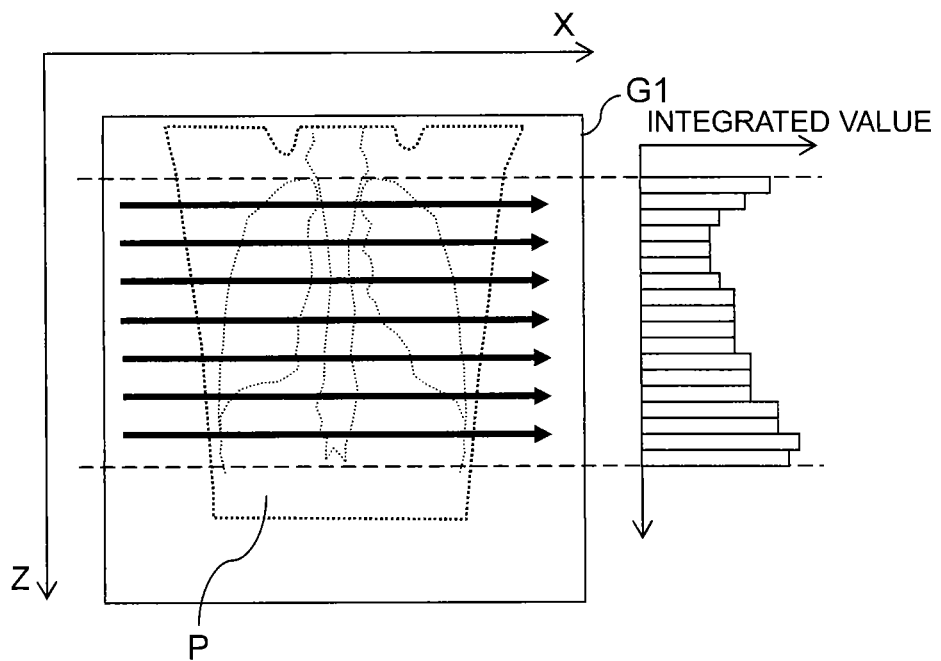
FIG. 6 is a diagram illustrating calculation processing for obtaining integrated values of pixel values from the plan scanogram shown in FIG. 2.

Specifically, as shown in FIG. 6, the current-value calculator 13 adds up the values of pixels in the X direction in the plan image G1 and repeats this for each of pixel lines arranged in the Z direction. Thereby, the current-value calculator 13 calculates the diameter (water-equivalent thickness) of a water phantom (a phantom filled with water) approximate to the examinee P. Then, the current-value calculator 13 calculates a tube current which allows the preset noise level to be obtained with the water phantom diameter while a scan method (e.g., multislice scan or helical scan) is taken into consideration.

The conversion-ratio calculator 14 uses the offset amount ΔL calculated by the correction-amount calculator 11 to predict a plan image in which the center position of the examinee P on the table 2a in the thickness direction coincides with the image center O1 of the side image G2 (the center position in the side image G2 in the upward-downward moving direction of the table 2a). Then, the conversion-ratio calculator 14 calculates, as a conversion ratio, a ratio (a magnification percentage or a reduction percentage) between the plan image thus predicted and the plan image G1 previously taken.

For example, when the center position of the examinee P in the thickness direction is located below the image center O1 (see FIG. 5), the table 2a is moved upward by the offset amount ΔL and therefore gets closer to the X-ray irradiator 3a. Accordingly, a plan image to be obtained after the table 2a is moved is larger than the plan image G1 taken before the table 2a is moved. For this reason, the magnification ratio of the image is obtained as the conversion ratio. On the other hand, when the center position of the examinee P in the thickness direction is located above the image center O1, the table 2a is moved downward by the offset amount ΔL and therefore gets away from the X-ray irradiator 3a. Accordingly, a plan image to be obtained after the table 2a is moved is smaller than the plan image G1 taken before the table 2a is moved. For this reason, the reduction ratio of the image is obtained as the conversion ratio.

The current-value convertor 15 converts the integrated values calculated by the current-value calculator 13 into estimated integration values based on the conversion ratio calculated by the conversion-ratio calculator 14. The current-value convertor 15 obtains the diameter (water-equivalent thickness) of a water phantom approximate to the examinee P by using the estimated integration values thus converted, and, as described above, calculates a tube current which allows the preset noise level to be obtained with the water phantom diameter while a scan method (e.g., multislice scan or helical scan) is taken into consideration.

Although the integrated values are directly converted into the estimated integrated values based on the calculated conversion ratio above, it is not limited this. For example, an integrated-value table may be saved for each conversion ratio, and an integrated-value table corresponding to a calculated conversion ratio may be selected and used.

These units of the controller 4a may be formed by hardware such as an electrical circuit, by software such as a program implementing their functions, or by a combination of both.

Next, a description is given of processing for adjusting a tube current, which is performed by the X-ray image diagnosis apparatus 1.

Figure 7:
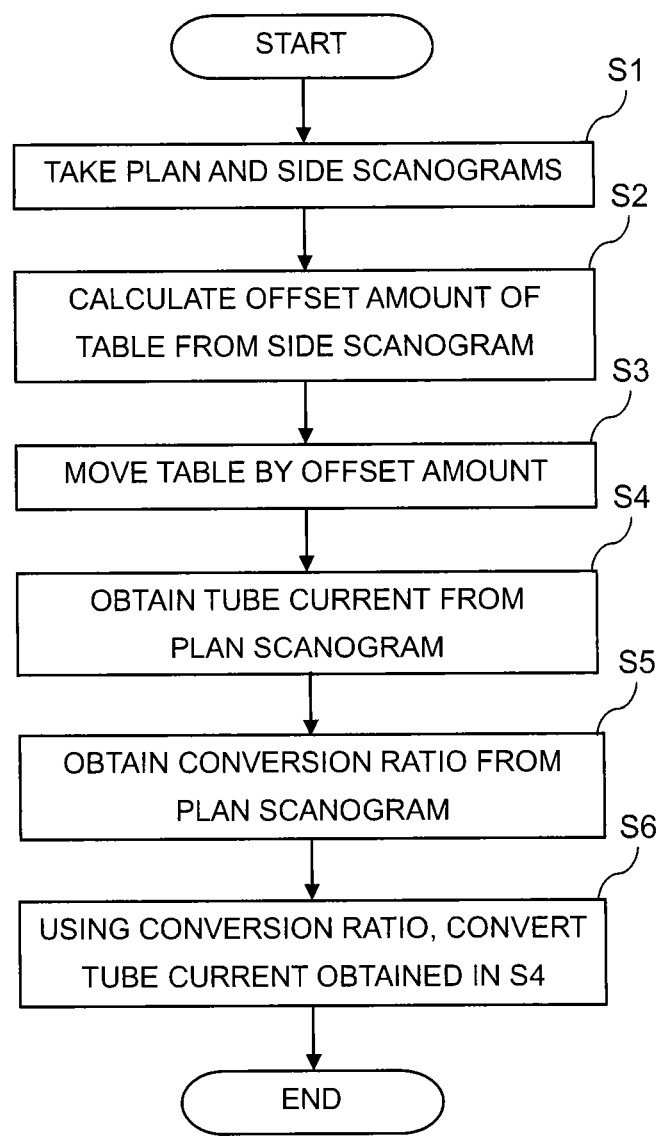
FIG. 7 is a flowchart showing the flow of processing for adjusting the position of a table and a tube current, which is performed by the X-ray image diagnosis apparatus shown in FIG. 1.

As shown in FIG. 7, first, plan and side scanograms are taken (Step S1). In this Step S1, the imaging device 3 images the examinee P at view-angle positions of 0° (plan position) and 90° (side position). For example, the irradiation field is set to maximum in this imaging. The plan image G1 (see FIG. 2) as a plan scanogram and the side image G2 (see FIG. 3) as a side scanogram are obtained as a result of this imaging, and they are displayed on the display 4e and saved in the storage 4c.

After Step S1, the offset amount ΔL, of the table 2a is calculated from the side scanogram (Step S2). In this Step S2, the correction-amount calculator 11 obtains the height position of the table 2a and the thickness of the examinee P from the side image G2 which is a side scanogram, and thus calculates the offset amount ΔL to be used to place the examinee P at the center of the FOV (see the description given above for details).

Figure 8:
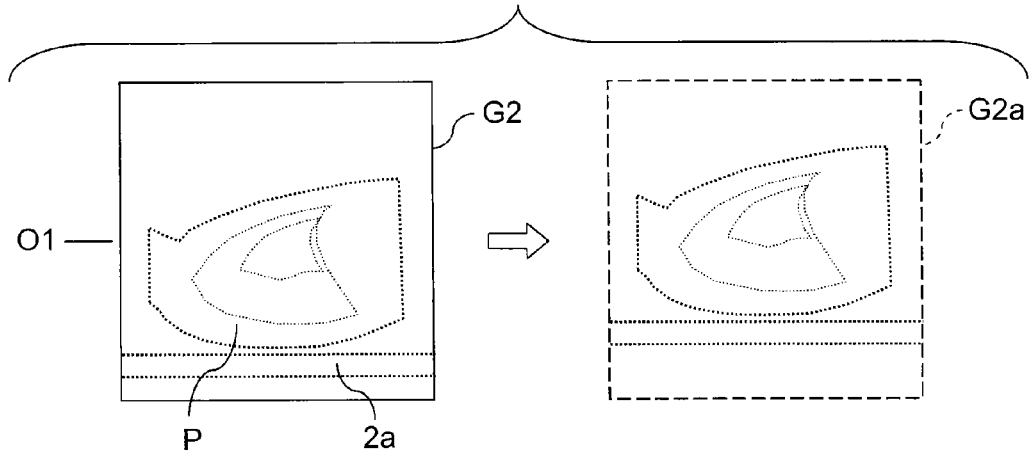
FIG. 8 is a diagram illustrating a state where the table is moved upward in the processing for adjusting the table position and the tube current shown in FIG. 7.

After Step S2, the table 2a is moved by the offset amount ΔL (Step S3). In this Step S3, the table controller 12 uses the offset amount ΔL calculated by the correction-amount calculator 11 to control upward and downward movement of the table 2a so that the center position of the examinee P on the table 2a in the thickness direction coincides with the image center O1 of the side image G2. As shown in FIG. 8, when the center position of the examinee P in the thickness direction coincides with the image center O1, the examinee P is located at the center of the FOV in a side image G2a which is a predicted image. In this way, the examinee P can easily be placed at the center of the FOV. Further, since the positioning of the examinee P is not dependant on the operator, the reproducibility of examination can be improved.

After Step 3, a tube current is obtained from the plan scanogram (Step S4). In this Step S4, an integrated value (an integrated amount) is calculated for each pixel line from the plan image G1 which is a plan scanogram. Then, from the integrated values, the diameter of a water phantom approximate to the examinee P is calculated, and a tube current which allows a desired noise level to be obtained with the water-phantom diameter by a certain scan method is calculated. Thereby, an X-ray amount appropriate for the body thickness of each part of the examinee P is automatically calculated to allow detailed control of the X-ray amount for each rotation. Accordingly, while maintaining high image quality, unnecessary radiation exposure is suppressed to achieve reduction in radiation exposure.

After Step S4, a conversion ratio is obtained from the plan scanogram (Step S5). In this Step S5, the offset amount ΔL calculated by the correction-amount calculator 11 is used to predict a plan image in which the center position of the examinee P on the table 2a in the thickness direction coincides with the image center O1 of the side image G2. Then, a ratio (a magnification percentage or a reduction percentage) between the plan image thus predicted and the plan image G1 previously taken is calculated as a conversion ratio.

Figure 9:
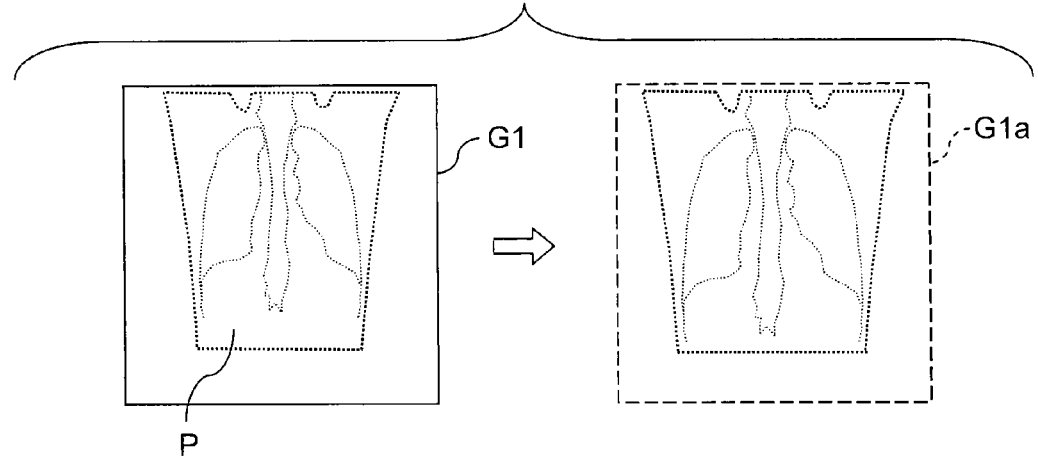
FIG. 9 is a diagram illustrating enlargement of the plan image in the processing for adjusting the table position and the tube current shown in FIG. 7.

For example, when the table 2a is moved upward to get closer to the X-ray irradiator 3a as shown in FIG. 8, a plan image G1a which is an image predicted to be obtained after the table 2a is moved is, as shown in FIG. 9, larger than the plan image G1 taken before the table 2a is moved. For this reason, the magnification ratio of the image is obtained as the conversion ratio. On the other hand, when the table 2a is moved downward to get away from the X-ray irradiator 3a, a plan image to be obtained after the table 2a is moved is smaller than the plan image G1 taken before the table 2a is moved. For this reason, the reduction ratio of the image is obtained as the conversion ratio.

After Step S5, the tube current is converted using the conversion ratio obtained (Step S6). In this Step S6, the integrated values are converted into an estimated integrated values based on the conversion ratio calculated by the conversion-ratio calculator 14, and these estimated integrated values are used to obtain the diameter of a water phantom approximate to the examinee P. Then, a tube current which allows a desired noise level to be obtained with the water phantom diameter by a given scan method is calculated. Thereby, an optimum tube current to be applied when the center position of the examinee P on the table 2a in the thickness direction coincides with the image center O1 of the side image G2 can be obtained. Consequently, since an optimum tube current can be obtained without retaking a plan image after adjustment of the height of the table 2a, increase in the amount of radiation exposure of the examinee P can be suppressed.

As described above, according to this embodiment, upward and downward movement of the table 2a is controlled to make the center position of the examinee P on the table 2a in the thickness direction coincide with the center position in the side image G2 in the upward-downward direction of the table 2a (i.e., with the image center O1 of the side image G2). This facilitates placement of the examinee P at the center of the effective field of view (FOV), and the positioning of the examinee P is not dependent on the operator. Thus, while achieving reduction in radiation exposure, the reproducibility of examination can be improved.

Further, the thickness of the examinee P is calculated from the side image G2 by using the height position of the table 2a acquired. Then, based on the thickness of the examinee P, the center position of the examinee P on the table 2a in the thickness direction is obtained to calculate a correction amount (the offset amount ΔL) for correcting the height position of the table 2a. Thus, the correction amount can be calculated based on the accurate center position of the examinee P in the thickness direction, and therefore the reproducibility of examination can be improved more reliably.

Moreover, the thickness of the examinee P is calculated by first bisecting the side image G2 at a center position of the side image G2 in the upward-downward moving direction of the table 2a and by adding a distance between the center position of the side image G2 and the height position of the table 2a and a distance between the center position of the side image G2 and the body surface of the examinee P. Thus, the thickness of the examinee P can be obtained accurately, and consequently, the correction amount can be calculated using an accurate center position of the examinee P in the thickness direction. Thus, the reproducibility of examination can be improved more reliably. Further, compared to a case where the thickness of the examinee P is calculated without bisecting the side image G2, the thickness of the examinee P can be calculated with a shorter time when the side image G2 is bisected. This allows reduction of the processing time.

Further, a conversion ratio used for conversion of a tube current (a value of a current for X-ray irradiation) is calculated according to the height position at which the table 2a is to be located when the center position of the examinee P on the table 2a in the thickness direction coincides with the center position in the side image G2 in the upward-downward moving direction of the table 2a, and the tube current is converted using the conversion ratio thus calculated. Accordingly, an optimum tube current can be obtained without retaking a plan image after adjustment of the height of the table 2a, and therefore increase in the amount of radiation exposure of the examinee P can be suppressed.

In addition, based on a relation between the height position at which the table 2a is located when the plan image G1 is taken and the height position at which the table 2a is to be located when the center position of the examinee P on the table 2a in the thickness direction coincides with the center position the side image G2 in the upward-downward moving direction of the table 2a, the magnification ratio or the reduction ratio of the plan image G1 is obtained as the conversion ratio. Thus, an accurate conversion ratio can be obtained. Accordingly, an optimum tube current can be accurately obtained, and therefore reduction in radiation exposure can be achieved more reliably.

Further, the water-equivalent thickness of a water phantom approximate to the size of the examinee P is obtained from the plan image G1, and a tube current (a value of a current applied for X-ray irradiation) which allows a predetermined noise level to be obtained with the water-equivalent thickness of the water phantom calculated. Accordingly, an optimum tube current can be accurately obtained, and therefore reduction in radiation exposure can be achieved more reliably.

Although the scanograms are taken at view angle positions of 0° (plan position) and 90° (side position) in the embodiment described above, the present invention is not limited to this. For example, the scanograms may be taken at view angle positions of 180° (plan position) and 270° (side position). When the view angle is 180°, X-rays are applied to the lower surface of the examinee P on the table 2a, and X-rays transmitted through the examinee P are detected.

Further, although the above-described image processing is performed directly on the scanograms (the plan image G1 and the side image G2) in the embodiment described above, the present invention is not limited to this. For example, smoothing processing may be performed on the scanograms or on the original images (raw data before image reconstruction) of the scanograms, and the image processing may be performed on those smoothed images. In these cases, values such as a correction amount and a conversion ratio can be obtained more accurately, and therefore the reproducibility of examination can be improved reliably. As the smoothing processing, various methods of smoothing processing for smoothing images can be used.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray image diagnosis apparatus comprising:
   a table on which an examinee lies down;
   a table driving unit configured to move the table upward and downward;
   an imaging device configured to take a side image of the examinee by irradiating a side of the examinee on the table with X-rays and detecting X-rays transmitted through the examinee or a plan image of the examinee by irradiating an upper or lower surface of the examinee on the table with X-rays and detecting X-rays transmitted through the examinee; and
   a controller including
      a current-value calculator configured to use the plan image to obtain a current value supplied to the imaging device for X-ray irradiation;
      a conversion-ratio obtaining unit configured to obtain a conversion ratio used to convert the current value according to a difference between a center position of the examinee on the table in thickness of the examinee in an upward-downward moving direction of the table and a center position of the side image in the upward-downward moving direction of the table; and
      a current-value convertor configured to convert the current value by using the conversion ratio.

2. The X-ray image diagnosis apparatus according to claim 1, wherein
   the controller subjects the side image to smoothing processing to generate a smoothed side image, and controls the table driving unit so that the table driving unit moves the table upward or downward to make the center position of the examinee on the table in the thickness direction coincide with a center position of the smoothed side image in the upward-downward moving direction of the table.

3. The X-ray image diagnosis apparatus according to claim 1, wherein
   the conversion-ratio obtaining unit is configured to obtain any one of a magnification ratio and a reduction ratio of the plan image as the conversion ratio based on a relation between a height position at which the table is located when the plan image is taken and a height position indicating the difference between the center position of the examinee on the table in the thickness of the examinee in the upward-downward moving direction of the table and the center position of the side image in the upward-downward moving direction of the table.

4. The X-ray image diagnosis apparatus according to claim 1, wherein
   the current-value calculator obtains, from the plan image, a water-equivalent thickness of a water phantom approximate to a size of the examinee, and obtains the current value which allows a predetermined noise level to be obtained with the water-equivalent thickness of the water phantom.

5. The X-ray image diagnosis apparatus according to claim 1, wherein the controller is configured to control the table driving unit so that the table driving unit moves the table upward or downward to make a center position of the examinee on the table in a thickness direction of the examinee coincide with a center position of the side image in an upward-downward moving direction of the table.

6. The X-ray image diagnosis apparatus according to claim 5, wherein
the controller acquires a height position of the table, and controls the table driving unit by using this height position of the table so that the table driving unit moves the table upward or downward to make the center position of the examinee on the table in the thickness direction coincide with the center position of the side image in the upward-downward moving direction of the table.

7. The X-ray image diagnosis apparatus according to claim 6, wherein
the controller includes:
a correction-amount calculator configured to acquire the height position of the table, calculate a thickness of the examinee from the side image by using the height position of the table, obtain the center position of the examinee on the table in the thickness direction based on the thickness of the examinee, and thus calculates a correction amount for correcting the height position of the table; and
a table controller configured to control the table driving unit so that the table driving unit moves the table upward or downward based on the correction amount.

8. The X-ray image diagnosis apparatus according to claim 7, wherein
the correction-amount calculator calculates the thickness of the examinee by first bisecting the side image at its center position in the upward-downward moving direction of the table, and then adding a distance between the center position of the side image and the height position of the table and a distance between the center position of the side image and a body surface of the examinee.

9. The X-ray image diagnosis apparatus according to claim 8, wherein
the controller subjects the side image to smoothing processing to generate a smoothed side image, and controls the table driving unit so that the table driving unit moves the table upward or downward to make the center position of the examinee on the table in the thickness direction coincide with a center position of the smoothed side image in the upward-downward moving direction of the table.

10. The X-ray image diagnosis apparatus according to claim 8, wherein
the conversion-ratio obtaining unit is configured to obtain any one of a magnification ratio and a reduction ratio of the plan image as the conversion ratio based on a relation between a height position at which the table is located when the plan image is taken and a height position indicating the difference between the center position of the examinee on the table in the thickness of the examinee in the upward-downward moving direction of the table and the center position of the side image in the upward-downward moving direction of the table.

11. The X-ray image diagnosis apparatus according to claim 8, wherein
the current-value calculator obtains, from the plan image, a water-equivalent thickness of a water phantom approximate to a size of the examinee, and obtains the current value which allows a predetermined noise level to be obtained with the water-equivalent thickness of the water phantom.

12. The X-ray image diagnosis apparatus according to claim 7, wherein
the controller subjects the side image to smoothing processing to generate a smoothed side image, and controls the table driving unit so that the table driving unit moves the table upward or downward to make the center position of the examinee on the table in the thickness direction coincide with a center position of the smoothed side image in the upward-downward moving direction of the table.

13. The X-ray image diagnosis apparatus according to claim 7, wherein
the conversion-ratio obtaining unit is configured to obtain any one of a magnification ratio and a reduction ratio of the plan image as the conversion ratio based on a relation between a height position at which the table is located when the plan image is taken and a height position indicating the difference between the center position of the examinee on the table in the thickness of the examinee in the upward-downward moving direction of the table and the center position of the side image in the upward-downward moving direction of the table.

14. The X-ray image diagnosis apparatus according to claim 7, wherein
the current-value calculator obtains, from the plan image, a water-equivalent thickness of a water phantom approximate to a size of the examinee, and obtains the current value which allows a predetermined noise level to be obtained with the water-equivalent thickness of the water phantom.

15. The X-ray image diagnosis apparatus according to claim 6, wherein
the controller subjects the side image to smoothing processing to generate a smoothed side image, and controls the table driving unit so that the table driving unit moves the table upward or downward to make the center position of the examinee on the table in the thickness direction coincide with a center position of the smoothed side image in the upward-downward moving direction of the table.

16. The X-ray image diagnosis apparatus according to claim 6, wherein
the conversion-ratio obtaining unit is configured to obtain any one of a magnification ratio and a reduction ratio of the plan image as the conversion ratio based on a relation between a height position at which the table is located when the plan image is taken and a height position indicating the difference between the center position of the examinee on the table in the thickness of the examinee in the upward-downward moving direction of the table and the center position of the side image in the upward-downward moving direction of the table.

17. The X-ray image diagnosis apparatus according to claim 6, wherein
the current-value calculator obtains, from the plan image, a water-equivalent thickness of a water phantom approximate to a size of the examinee, and obtains the current value which allows a predetermined noise level to be obtained with the water-equivalent thickness of the water phantom.

18. The X-ray image diagnosis apparatus according to claim 5, wherein the controller subjects the side image to smoothing processing to generate a smoothed side image, and controls the table driving unit so that the table driving unit moves the table upward or downward to make the center position of the examinee on the table in the thickness direction coincide with a center position of the smoothed side image in the upward-downward moving direction of the table.

19. The X-ray image diagnosis apparatus according to claim 5, wherein the conversion-ratio obtaining unit is configured to obtain any one of a magnification ratio and a reduction ratio of the plan image as the conversion ratio based on a relation between a height position at which the table is located when the plan image is taken and a height position indicating the difference between the center position of the examinee on the table in the thickness of the examinee in the upward-downward moving direction of the table and the center position of the side image in the upward-downward moving direction of the table.

20. The X-ray image diagnosis apparatus according to claim 5, wherein the current-value calculator obtains, from the plan image, a water-equivalent thickness of a water phantom approximate to a size of the examinee, and obtain the current value which allows a predetermined noise level to be obtained with the water-equivalent thickness of the water phantom.

* * * * *